(12) United States Patent
Kleckner et al.

(10) Patent No.: US 8,578,118 B2
(45) Date of Patent: Nov. 5, 2013

(54) SCHEME FOR OVERWRITING STORED PHYSIOLOGICAL DATA IN AN IMPLANTABLE MEDICAL DEVICE

(75) Inventors: Karen J. Kleckner, New Brighton, MN (US); Paul G. Krause, Shoreview, MN (US); Traci K. Washburn, Roseville, MN (US); Melinda A. Kolstad, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1496 days.

(21) Appl. No.: 11/740,362

(22) Filed: Apr. 26, 2007

(65) Prior Publication Data

US 2008/0269811 A1    Oct. 30, 2008

(51) Int. Cl.
    *G06F 12/00* (2006.01)
(52) U.S. Cl.
    USPC ............. 711/170; 711/221; 711/E12.014; 607/2; 607/59; 607/60; 600/301
(58) Field of Classification Search
    None
    See application file for complete search history.

(56) References Cited

U.S. PATENT DOCUMENTS

| | | | |
|---|---|---|---|
| 4,374,382 A | 2/1983 | Markowitz | |
| 5,513,645 A | 5/1996 | Jacobson et al. | |
| 5,944,745 A | 8/1999 | Rueter et al. | |
| 5,987,352 A | 11/1999 | Klein et al. | |
| 6,027,456 A * | 2/2000 | Feler et al. | 600/554 |
| 6,134,474 A | 10/2000 | Fischell et al. | |
| 6,480,745 B2 | 11/2002 | Nelson et al. | |
| 6,522,915 B1 | 2/2003 | Ceballos et al. | |
| 6,526,314 B1 | 2/2003 | Eberle et al. | |
| 6,535,765 B1 | 3/2003 | Amely-Velez et al. | |
| 6,589,187 B1 * | 7/2003 | Dirnberger et al. | 600/508 |
| 6,912,483 B2 * | 6/2005 | Frederick | 702/187 |
| 7,130,678 B2 | 10/2006 | Ritscher et al. | |
| 7,484,129 B1 * | 1/2009 | Varrichio | 714/42 |
| 2004/0044836 A1 | 3/2004 | Wong et al. | |
| 2005/0283210 A1 * | 12/2005 | Blischak et al. | 607/60 |

FOREIGN PATENT DOCUMENTS

WO      WO2006050360 A      5/2006

OTHER PUBLICATIONS

"Definition of Variable", 1913, Webster's Dictionary.*
Dictionary.com, "Definie Periodic at Dictionary.com", Apr. 21, 2013.*
International Search Report, PCT/US2008/059205, Aug. 14, 2008, 5 Pages.

* cited by examiner

*Primary Examiner* — Reginald Bragdon
*Assistant Examiner* — Eric Loonan
(74) *Attorney, Agent, or Firm* — Michael C. Soldner

(57) ABSTRACT

An implantable medical device and associated method store physiological data in response to detecting a physiological event. The medical device includes multiple first memory locations allocated to each of a number of physiological event types and a second single memory location allocated for storing entries of physiological signal data corresponding to each of the plurality of physiological event types.

22 Claims, 11 Drawing Sheets

SCHEME FOR OVERWRITING STORED PHYSIOLOGICAL DATA IN AN IMPLANTABLE MEDICAL DEVICE

TECHNICAL FIELD

The invention relates generally to implantable medical devices and, in particular, to an automatic method for managing physiological data storage.

BACKGROUND

Numerous implantable medical devices (IMDs) are configured for monitoring and storing physiological data for use in diagnosing a patient condition or managing medical therapies. Such devices include implantable cardiac pacemakers, implantable cardioverter defibrillators (ICDs), hemodynamic monitors, subcutaneous ECG monitors, neural stimulators, and the like. Detection of a physiological event, such as an arrhythmia, generally triggers storage of summary information relating to the event in an episode log and detailed physiological signal data is stored in an episode record, e.g. the ECG signal over an interval of time including the event detection and corresponding marker channel data. Such physiological signal storage is useful to a clinician in diagnosing patient condition and managing patient therapies. An IMD may be capable of detecting numerous types of physiological events based on sensed signals but generally has limited memory capacity for storing data relating to detected physiological events due to physical size constraints.

Storage of a physiological signal in an episode record requires considerably more memory than storage of summary data in an episode log. In order to ensure that the episodes stored in an episode log and episodes stored in an episode record correspond to each other and are available for interrogation, IMD memory is typically allocated separately for episode logs and episode records for each of a number of a different types of physiological events. However, a patient may experience multiple episodes of one event type and few or no episodes of other event types. As a result, memory allocated for storing episode records for one type of event may be under-allocated. The allocated memory may be quickly filled with new episodes overwriting old episodes of the same event type. Meanwhile, memory allocated for other rarely-occurring event types is underutilized. As implantable devices become smaller to avoid patient discomfort and ease implant procedures, memory capacity becomes more limited, increasing the importance of efficient management of physiological data storage.

DETAILED DESCRIPTION

In the following description, references are made to illustrative embodiments for carrying out the invention. It is understood that other embodiments may be utilized without departing from the scope of the invention. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
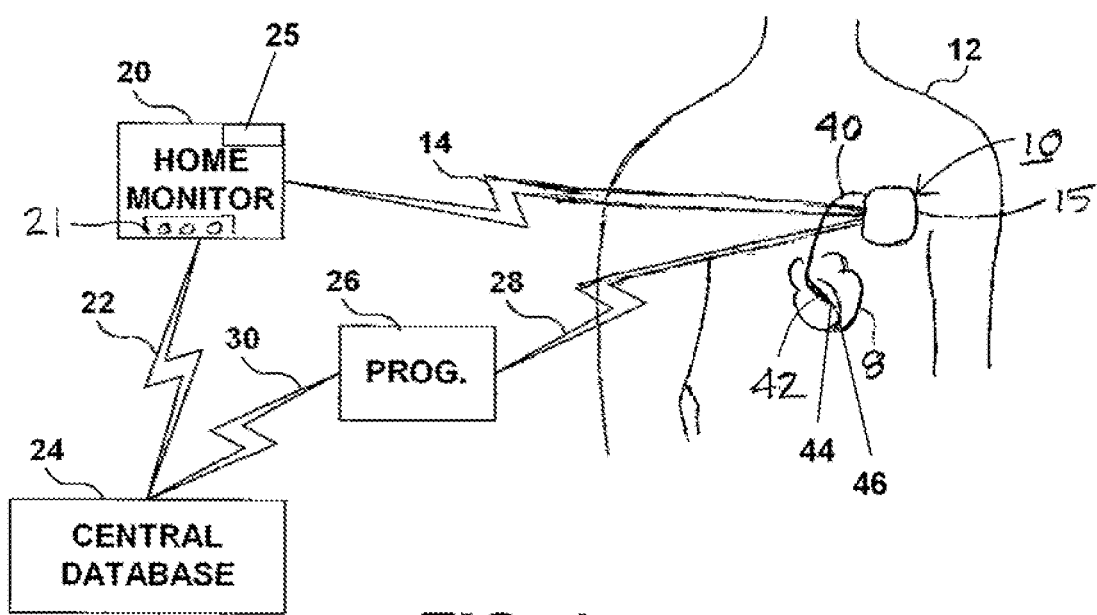
FIG. 1 illustrates an implantable medical device (IMD) system.

FIG. 1 illustrates an implantable medical device (IMD) system. IMD 10 is shown implanted in a patient 12. The simplified illustration of IMD 10 may represent a variety of IMDs such as a cardiac pacemaker, implantable cardioverter defibrillator, hemodynamic monitor, ECG recorder, or a drug delivery device. In alternative embodiments, IMD 10 may be implemented as an glucose monitor, insulin pump, or a neurological stimulator. IMD 10 may be coupled to one or more fluid delivery catheters or electrical leads 40. Lead 40 is used for carrying electrodes or physiological sensors used for monitoring one or more physiological signals and delivering electrical stimulation therapies to the patient's heart 8. The IMD 10 may also be embodied with one or more subcutaneous leads for carrying additional electrodes and/or physiological sensors. Furthermore, the IMD 10 may communicate via telemetry within the body of patient 12 with remotely placed sensors. IMD 10 may alternatively be embodied as a leadless device wherein sensors and/or electrodes are incorporated in or on the housing 15 of IMD 10. One example of a subcutaneous monitoring device in which aspects of the present invention may be embodied is generally disclosed in U.S. Pat. No. 5,987,352 issued to Klein et al, hereby incorporated herein by reference in their entirety.

Lead 40 is shown as a ventricular lead including a coil electrode 42. Coil electrode 42 may be used in conjunction with IMD housing 15 for delivering cardioversion/defibrillation shocks to a patient. Lead 40 may also be provided with a tip electrode 46 and a ring electrode (not shown) for sensing ventricular signals and delivering cardiac pacing pulses. Lead 40 is shown positioned in the right ventricle, however a ventricular lead may alternatively be positioned in operative relation to the left ventricle, for example in a cardiac vein via the coronary sinus. In dual chamber and multichamber devices, leads may be positioned in one or both atrial chambers as well as one or both ventricular chambers.

In the embodiment shown, lead 40 further includes a blood pressure sensor 44. In other embodiments, lead 40 or other additional leads may be provided including other physiological sensors, e.g. blood chemistry sensors, temperature sensors, optical sensors, flow sensors, wall motion sensors or the like. Furthermore, while IMD 10 is shown as a cardiac device coupled to the patient's heart 8 via lead 40, various embodiments of the invention may include other types of implantable medical devices configured to monitor a physiological signal and detecting a condition or event associated with a change in the monitored signal or a parameter derived therefrom.

IMD 10 is provided with an antenna and associated circuitry, as will be described below, for establishing a communication link 14 with external telemetry circuitry 25 included in home monitor 20. Home monitor 20 may include a user interface 21 that allows patient 12 or other caregiver to transmit commands or signals to IMD 10 using home monitor 20, for example commands which trigger physiological data storage by IMD 10. Home monitor 20 may be configured to receive data from IMD 10 for transmission to a central database 24 to enable remote monitoring of patient 12. In some embodiments, home monitor 20 may be selectively enabled to program an operating mode or control parameters used by IMD 10. Home monitor 20 may be embodied as a bedside or table top unit, a handheld unit or a wearable device.

IMD 10 is further enabled for bidirectional communication with a physician programmer 26 via telemetry link 28. Physician programmer 26 is generally located in a health care facility, such as a clinic or hospital, for use by medical personnel and is typically enabled for full programming and interrogation functionality.

Home monitor 20 and/or programmer 26 may optionally be adapted to communicate with a central database 24 to allow transfer of data received from IMD 10 to the central database 24. A central database may be an Internet-based or other networked database used for remote patient monitoring. Home monitor 20 may transfer data via a communication link 22, which may be established via the Internet, a local area network, a wide area network, a telecommunications network or other appropriate communications network and may be a wireless communication link. Likewise, programmer 26 may receive data from IMD 10 and transfer the data to central database 24 using a communication link 30. In this way, physiological data stored in response to detecting physiological events can be transmitted to home monitor 20 or programmer 26 and one to central database 24 for review by a clinician. One example of a remote patient monitoring system is generally disclosed in U.S. Pat. No. 6,480,745 (Nelson et al.), hereby incorporated herein by reference in their entirety.

Figure 2:
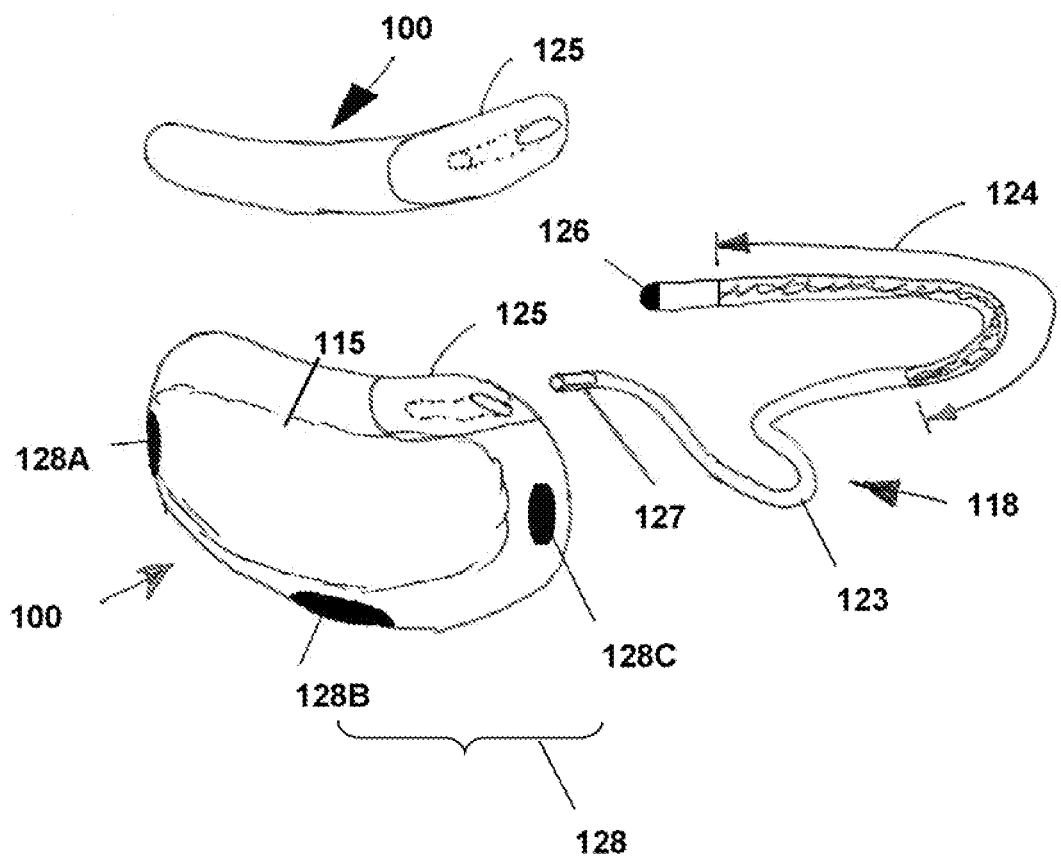
FIG. 2 is a top and plan view of a subcutaneous ICD, which operates without the use of transvenous intracardiac leads.

FIG. 2 is a top and plan view of a subcutaneous ICD 100, which operates without the use of transvenous intracardiac leads. Subcutaneous ICD 100, referred to hereafter as SubQ ICD 100, illustrates another type of IMD in which methods described herein for managing storage of physiological data may be implemented. SubQ ICD 100 includes a generally ovoid housing 115 having a substantially kidney-shaped profile. The plan view shows the generally ovoid construction of housing 115 that promotes ease of subcutaneous implant. This structure is ergonomically adapted to minimize patient discomfort during normal body movement and flexing of the thoracic musculature. Connector block 125 is coupled to housing 115 for receiving the connector assembly 127 of subcutaneous lead 118.

Subcutaneous lead 118 includes distal coil electrode 124, distal sensing electrode 126, which may be configured as a tip electrode or ring electrode, an insulated flexible lead body 123 and a proximal connector assembly 127 adapted for connection to SubQ ICD 100 via connector block 125. Distal sensing electrode 126 is sized appropriately to match the sensing impedance of a housing-based subcutaneous electrode array (SEA) 128. SEA 128 includes multiple electrodes 128A, 128B, and 128C mounted on the housing 115. Three electrodes 128A, 128B, and 128C, which may be positioned in an orthogonal arrangement, are included in SEA 128 in the embodiment shown in FIG. 2. Other embodiments of a SubQ ICD may include any number of electrodes mounted on or incorporated in housing 115. It is recognized that any combination of lead-based and/or housing based electrodes may be used for sensing subcutaneous ECG signals. Multiple subcutaneous electrodes are provided to allow multiple subcutaneous ECG sensing vector configurations.

The SEA electrodes 128A, 128B, and 128C are coupled to internal electronic circuitry (described herein below) inside housing 115. The electronic circuitry enclosed in SubQ ICD 100 is configured for detecting arrhythmias using sensed ECG signals using any of the electrodes in SEA 128 and electrode 126. SubQ ICD 100 provides cardioversion/defibrillation shocks using coil electrode 124 in response to detected tachycardias as needed as well as post-shock pacing using any of the SEA electrodes and electrode 126 if needed while the heart recovers. An example of a SubQ ICD is generally disclosed in U.S. Pat. No. 6,522,915 (Ceballos et al.), hereby incorporated herein by reference in its entirety.

Figure 3:
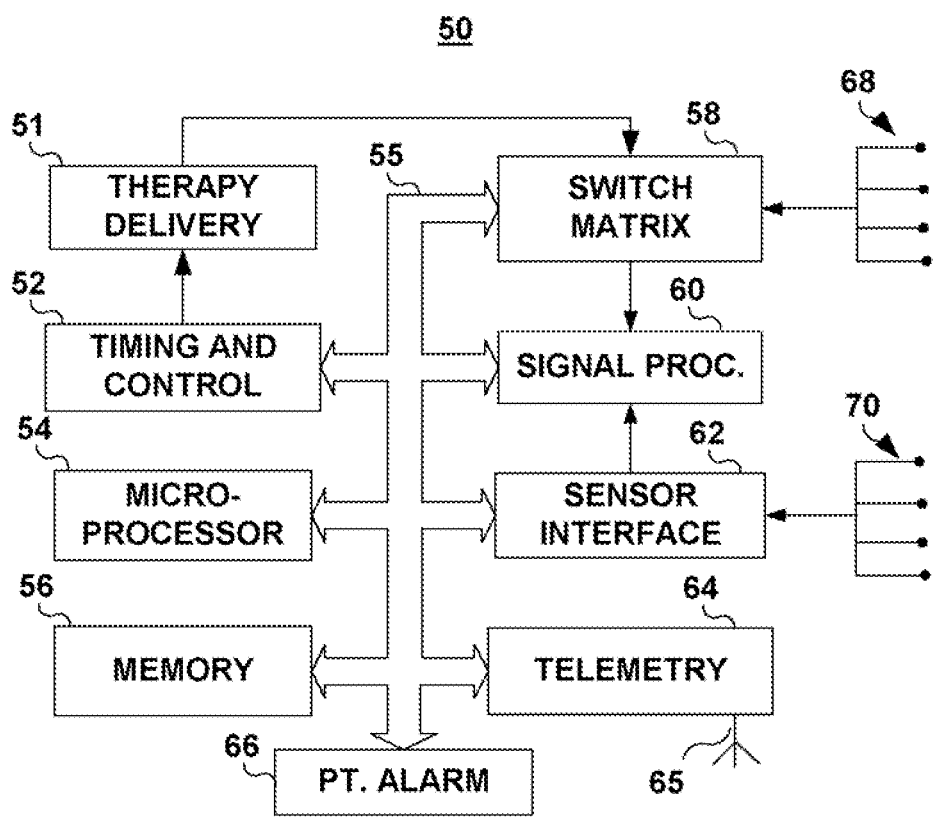
FIG. 3 is a functional block diagram of circuitry included in an IMD, such as the IMD shown in FIG. 1 or the subcutaneous ICD 100 shown in FIG. 2.

FIG. 3 is a functional block diagram of circuitry included in an IMD, such as IMD 10 shown in FIG. 1 or SubQ ICD 100 shown in FIG. 2. IMD circuitry 50 generally includes timing and control circuitry 52 and an operating system that may employ microprocessor 54 or a digital state machine for timing sensing and therapy delivery functions in accordance with a programmed operating mode. In various embodiments, control circuitry and other functional IMD circuitry may include an application specific integrated circuit (ASIC), an electronic circuit, a processor (shared, dedicated, or group) and memory that execute one or more software or firmware programs, a combinational logic circuit, or other suitable components that provide the described functionality.

Microprocessor 54 and associated memory 56 are coupled to the various components of IMD circuitry 50 via a data/address bus 55. IMD circuitry 50 may include therapy delivery unit 51 for delivering a therapy, such as an electrical stimulation or drug therapy, under the control of timing and control 52. In the case of electrical stimulation therapies, such as cardiac stimulation therapies, therapy delivery unit 51 is typically coupled to two or more electrodes 68 via a switch matrix 58. Switch matrix 58 is used for selecting which electrodes and corresponding polarities are used for delivering electrical stimulation pulses.

Electrodes 68 may correspond to lead-based electrodes, leadless electrodes incorporated on the IMD housing, and/or the IMD housing configured for use as a can or case electrode. Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog to digital converter. Electrical signals may then be used by microprocessor 54 for detecting physiological events, such as detecting and discriminating cardiac arrhythmias, detecting ischemia, detecting changes in heart rate variability, etc. Electrodes 68 may also be used for measuring impedance signals for monitoring edema, respiration, heart chamber volume or other physiological conditions that produce impedance-varying signals. Any of these signals may be used to detect a physiological event.

IMD 10 may additionally or alternatively be coupled to one or more physiological sensors 70. Such sensors may include pressure sensors, accelerometers, flow sensors, blood chemistry sensors, activity sensors, optical sensors, temperature sensors, or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions according to defined detection thresholds. Signals from sensors 70 and/or signals from electrodes 68 are used by microprocessor 54 for detecting events corresponding to a number of predetermined event types. IMD circuitry 50 is configured to log detected events according to event type, and store episode records of detected events for diagnostic purposes. Sensed ECG and other physiological sensor signals may also be used for sensing the need for delivering a therapy under control of the operating system.

The operating system includes associated memory 56 for storing operating commands and data for controlling device operation and for later retrieval of data stored to diagnose device function or patient condition. A portion of memory 56 is allocated for storing data compiled from sensed physiological signals and data relating to device operating history for telemetry out on receipt of a retrieval or interrogation instruction. IMD circuitry 50 is configured to monitor one or more physiological signals and detect physiological events therefrom. Detection of a physiological event according to programmed detection algorithm triggers the storage of event data. Triggered data storage is generally described in the above-incorporated Klein patent. As will be described in detail herein, a portion of memory 56 is configured for logging detected physiological events in separately allocated memory locations corresponding to each event type. Another portion of memory 56 is configured for storing episode records corresponding to all event types. A physiological event detection is logged in memory 56 by storing the date and time of the detected event in an episode log corresponding to the detected event type. Other summary data, such as parametric data relating to the event duration or other parameters derived from the physiological signal used for detecting the event, e.g. a heart rate, a maximum, minimum or average parameter value, or the like, may also be stored in the episode log.

Detection of a physiological event further triggers storage of more detailed physiological data in an episode record allocated in memory 56. The episode record generally includes a stream of the sampled physiological signal points over an interval of time including the time of the event detection. Marker channel data may also be stored in response to an event detection and incorporated in the episode record. Acquisition of marker channel data is generally described in U.S. Pat. No. 4,374,382 (Markowitz), hereby incorporated herein by reference in its entirety. Triggered storage of such physiological signal data in episode records requires greater memory capacity than the storage of summary event data in a episode log.

IMD circuitry 50 further includes telemetry circuitry 64 and antenna 65. Programming commands or data are transmitted during uplink or downlink telemetry between IMD telemetry circuitry 64 and external telemetry circuitry included in a programmer or home monitoring unit. The patient may be provided with an external device for use in transmitting a command to the implanted device. As such, telemetry 64 may be used to receive a patient-initiated command. In some embodiments of the invention, a patient can trigger storage of an episode record by using an external device in communication with telemetry circuitry 64. IMD circuitry 50 may be equipped with patient alarm circuitry 66 for generating audible tones, a perceptible vibration, muscle stimulation or other sensory stimulation for notifying the patient that an alarm condition has been detected.

Figure 4:
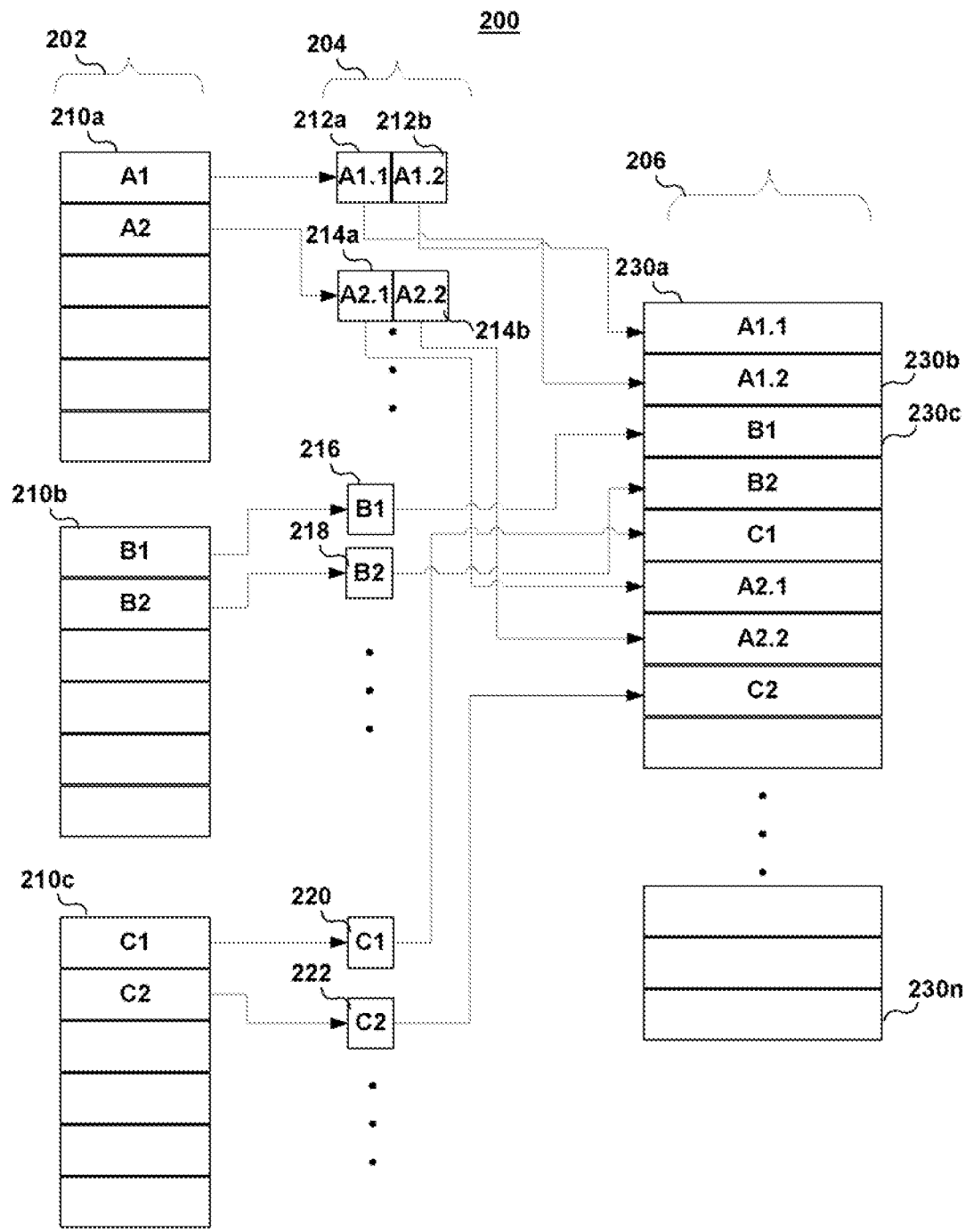
FIG. 4 is a schematic diagram of a memory structure used for storing physiological event data in an IMD.

FIG. 4 is a schematic diagram of a memory structure used for storing physiological event data in an IMD. Memory structure 200 includes a log 202, an allocation table 204 and an episode record 206. Log 202 includes a number of separately allocated episode logs 210a, 210b and 210c. Each of the separately allocated episode logs 210a, 210b and 210c are assigned to a unique physiological event type. A detected physiological event is logged in the episode log 210a, 210b or 210c assigned to the type of event detected. The number of episode logs will vary between applications and will depend on the number of event types that the IMD is configured to detect. In one embodiment, in an implantable device provided for monitoring arrhythmias using subcutaneous ECG signals, log 202 includes six episode logs allocated for storing six event types: ventricular tachycardia (VT), fast ventricular tachycardia (FVT), atrial fibrillation (AF), atrial tachycardia (AT), bradycardia, and asystole. An additional episode log may be allocated for logging the receipt of a patient-generated command for activating storage of physiological data. In another embodiment, a SubQ ICD is provided with six episode logs corresponding to treated VTNF episodes, untreated rhythm episodes, concerning episodes, asystole, bradycardia, and low amplitude sensing episodes.

Each of the episode logs 210a, 210b and 210c include a number of possible episode entries, with each entry including multiple fields for storing episode summary data upon detecting a physiological event. For example, each episode log 210a, 210b, and 210c may be allocated enough memory for storing anywhere from 5 to 50 episode entries. In other embodiments, more or less possible episode entries may be included in each log. In the example shown in FIG. 4, each log 210a, 210b, and 210c includes two logged entries corresponding to detected events: A1 and A2 in episode log 210a; B1 and B2 in episode log 210b; and C1 and C2 in episode log 210c.

Figure 5:
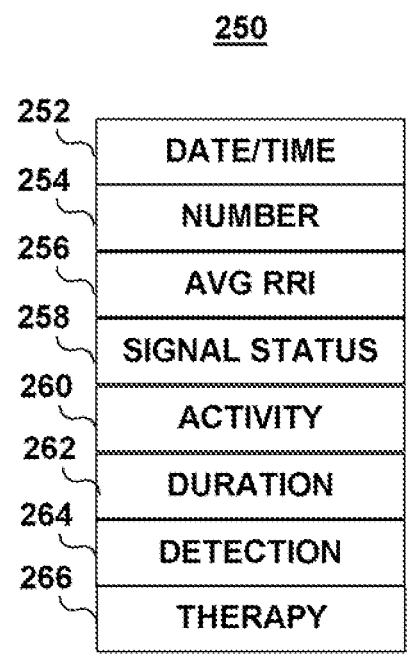
FIG. 5 is a diagram of one example of an episode log entry including multiple data fields.

Each entry in an episode log 210a through 210c includes a number of fields for storing specific summary data. FIG. 5 is a diagram of one example of an episode log entry 250 including multiple data fields 252 through 266. The number and types of fields included in each episode log entry will be defined according to a particular application. The episode log entry fields 252 through 264 are illustrative and generally include at least a date and time field 252 for storing the date and time the event was detected. The episode number is stored at block 254. The remaining fields 256 through 266 are more application specific. In one example, where ECG signals are monitored for detecting arrhythmia events, a field 256 may be provided for storing an average RR interval (interval between consecutively sensed R-waves in the ECG signal). The status of the sensed ECG signal may be stored in field 258 to indicate low amplitude sensing episodes. The patient activity level may be stored in field 260 as determined from an activity sensor. The duration of the detected episode is stored in field 262. Parameters used to detect the arrhythmia event may be stored in field 264. Field 266 is provided for entering any therapies that were delivered in response to the detected event. It is recognized that numerous variations in the number and types of fields included in an episode log entry will exist.

Referring again to FIG. 4, episode record 206 includes multiple segments 230a through 230n allocated for storing detailed records of physiological signals corresponding to a detected event. A single episode record 206 is allocated for storing episodes of all event types. In past practice, separate episode records and episode logs have been allocated for each type of event. However, space allocated for use in storing episode records for a particular event type may go unused if the patient never experiences that particular event type. Meanwhile, an episode record assigned to another frequently-detected event type may become full with episode record entries being overwritten in response to newly detected events. In the memory structure 200, one portion of memory, i.e. episode record 206, is allocated for storing episode record entries for all event types. All segments 230a through 230n can be fully utilized before any records become overwritten, regardless of the frequency of detecting the different event types. As such, the memory allocated for storing episode record entries is fully utilized prior to overwriting any entries.

Episode record 206 may be provided with, for example, 10 to 100 segments 230a through 230n with each segment capable of storing anywhere from a few seconds to one minute or more of physiological signal data. The number of segments and size of each segment will be defined according to a particular application and IMD capacity. In one embodiment, record 206 includes between 25 and 30 segments each storing about 1 minute of physiological signal data. In another embodiment, record 206 includes 60 segments each storing about 15 seconds of data.

The number of segments needed to store a particular episode will depend on the event type and the segment size. A single episode record entry may occupy, for example, 1 to 10 segments. The number of segments occupied by a single episode record entry is defined according to event type. For example, in one embodiment, an IMD may be configured to detect six types of events with three of the event types requiring one segment per episode record entry and the other three event types requiring two segments per episode record entry. A clinician may be interested in recording a longer interval of a physiological signal for certain events or certain events may require longer intervals of time for meeting detection requirements.

If an episode has a longer duration than the time available from the designated number of episode record segments, the episode record entry may be truncated or a data gap may inserted during episode record storage. Typically, a episode record entry will include a predetermined interval of time prior to the time of event detection and a period of time following the event detection. If the time from detection to termination exceeds the available memory in the designated number of episode record segments, a gap in the data may exist in order to record both the interval up to and including event detection and an interval including event termination.

In other embodiments, the number of segments used to store an episode record entry may be variable and determined "on-the-fly" as the episode is occurring. A maximum number of segments to be occupied by any one episode record entry may be specified.

In some embodiments, episode record 206 may be allocated for storing only device-detected episode record entries and a separately allocated episode record (not shown) may be provided for storing a predetermined number of patient-initiated episode record entries.

The allocation table 204 registers the segments in episode record 206 in which episode record entries are stored, providing a link to corresponding entries in episode logs 210a through 210c. Upon initial implant, all episode logs 210a through 210c and episode record segments 230a through 230n will be available for logging detected events and storing episode record entries. As physiological events are detected, according to programmed event detection algorithms, the events are logged in the appropriate episode log 210a through 210c and a corresponding episode record entry is written in episode record 206. The episode record entries may be stored in segments 230a through 230n in chronological order initially, i.e. as events are detected, episode records are stored, progressively filing up the segments 230a through 230n.

For example, in FIG. 4, a first detected event A1 is logged in episode log 210a. The A1 event is also recorded in episode record 206 using the first segments 230a and 230b. Entries 212a and 212b in allocation table 204 store the locations of entries A1.1 and A1.2 in the episode record 206 providing a link between the A1 log entry in episode log 210a and the A1 episode record entry involving the two segments 230a and 230b. When the IMD is interrogated, the log entry for the A1 event can be matched to the episode record segments corresponding to the same A1 event via allocation table 204. In this way, information stored in the log 202 can be presented with corresponding physiological signal data stored in episode record 206.

The next detected event B1 is logged in episode log 210b and physiological signal data is stored in the next available episode record segment 230c. Only one segment 230c is required for storing the episode record for the B1 event type. An entry 216 in the allocation table 204 provides a link between the logged event B1 in episode log 210b and the episode record entry in segment 230c for the same event, B1.

As events continue to be detected, entries are made in the appropriate event log 210a through 210c and episode records are stored in segments 230a through 230n as they occur. In the example shown in FIG. 4, event B1 is followed by event B2 of the same type, logged in episode log 210b with entry 218 in allocation table 204 storing the location of the episode record entry in episode record 206. Following event B2, an event C1 is logged in episode log C1, with an allocation table entry 220 storing the location of the corresponding episode record entry. Following event C1, another event A2 is logged in episode log 210a, requiring two segments A2.1 and A2.2 for storing the corresponding episode record entry. Corresponding allocation table entries 214a and 214b link the logged event A2 with the episode record segments A2.1 and A2.2. Finally an event C2 is logged in episode log 210c with a corresponding episode record entry in the next available episode record segment and a linking allocation table entry 222.

Episode record 206 will typically become full prior to any of episode logs 210a through 210c. As such, segments 230a through 230n may be used to store episode record entries in chronological order until all segments are used. After which, new episode record entries stored in response to newly detected episodes will overwrite previously stored episode record entries. Rather than merely "wrapping" the data in a "first-in-first-out" basis such that the chronologically oldest entry is overwritten by the newest entry, episode record entries are overwritten according to a set of priority rules for identifying candidate segments to be overwritten and then selecting a required number of the candidate segments to be overwritten by the new record. Generally, the number of possible episode log entries is allocated such that the number of episode log entries will always be likely to exceed the number of episode record entries. In this way, an episode record entry is likely to always have a link to a corresponding episode log entry (while each episode log entry may or may not be linked to an episode record entry).

Figure 6:
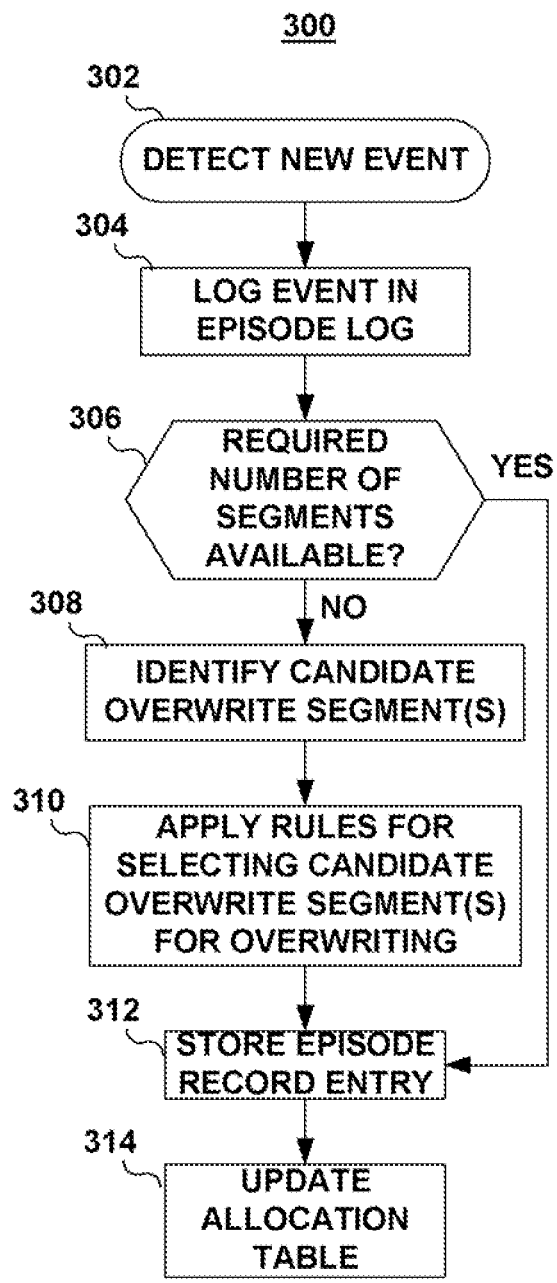
FIG. 6 is a flow chart of a method for storing data in an episode record.

FIG. 6 is a flow chart of a method 300 for storing data in an episode record. Flow chart 300 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 302, a new physiological event is detected according to programmed detection algorithms. The detected event is logged in the episode log corresponding to the event type at block 304. If the episode log is full, the oldest log entry is overwritten by the new event entry. A log entry may be initiated upon event detection with additional episode log fields being filled during the episode and/or upon detecting termination of the event, e.g. fields requiring information that is determined subsequent to event detection such as the episode duration and any delivered therapies. As will be further described below, a log entry may alternatively be written after detecting termination of the event allowing the event type to be discriminated or re-categorized while the episode is in progress.

A determination is made at decision block 306 whether the required number of segments are available that are needed to store an episode record entry corresponding to the newly detected event. One or more segments may be required depending on the event type. If the required number of segments is available, e.g. if the memory allocated for storing episode records has not yet been filled, an episode record entry is written to the required number of segments at block 312.

If the required number of segments is not available, candidate overwrite segments are identified at block 308. Segments are identified as overwrite candidates according to prioritized rules as will be further described below. At block 310, candidate selection rules are applied for selecting which identified overwrite candidate segments will be overwritten. The candidate selection rules applied may depend on the type of the newly detected event as well as the type of event previously stored in the candidate segments.

Once the candidate overwrite segments are selected, the episode record entry is stored at block 312 by overwriting the necessary number of segments to store the new entry. At block 314, the allocation table is updated. The allocation table entry linking the overwritten episode record entry to an episode log entry is cleared such that the link between the episode log entry and the overwritten episode record entry is broken. The episode log entry remains in the episode log such that the summary episode data is available upon device interrogation, however the detailed physiological signal data is no longer available. A new allocation table entry links the new episode log entry to the newly stored episode record entry.

Figure 7:
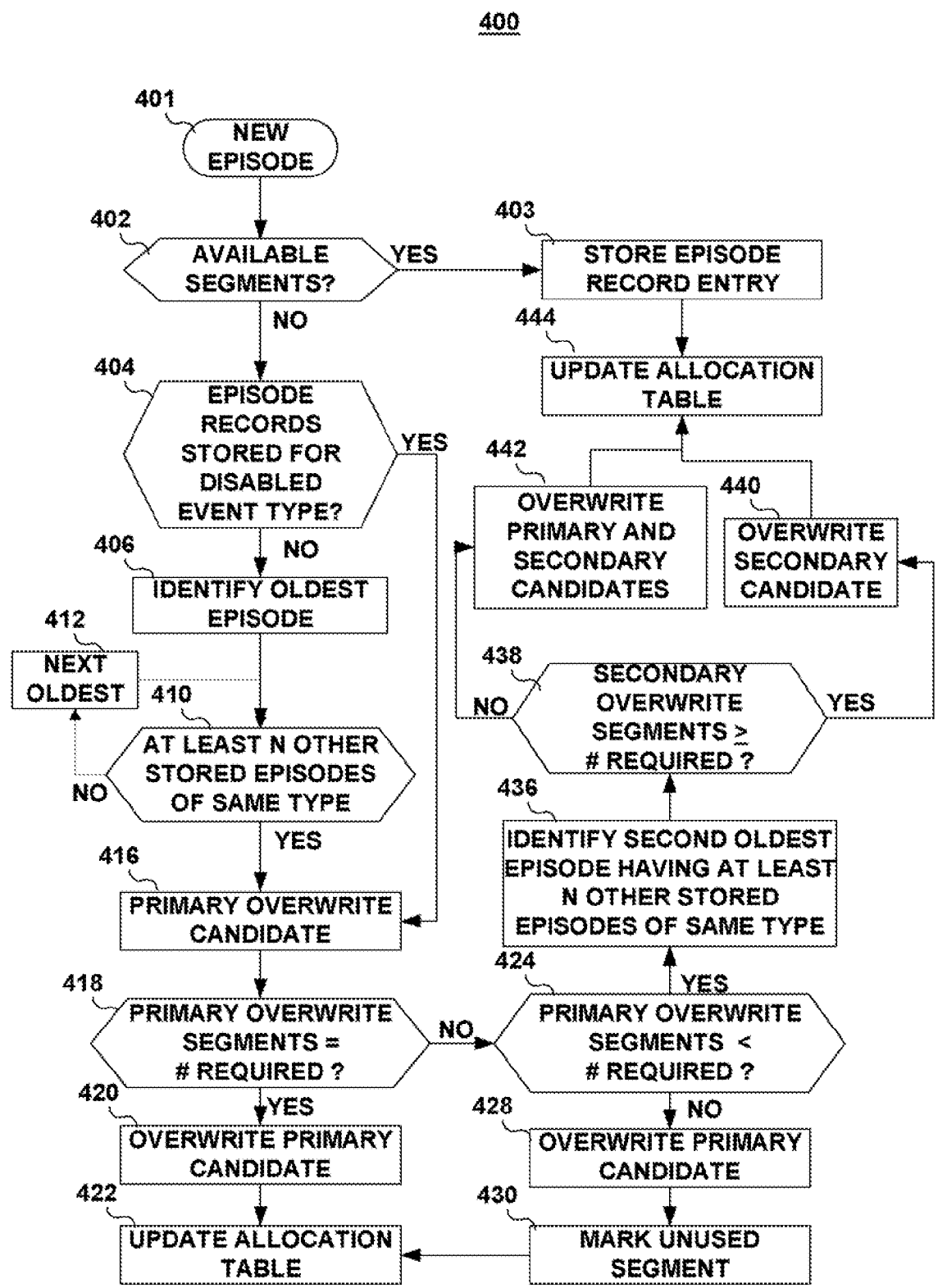
FIG. 7 is a flow chart of a method for identifying and selecting overwrite candidate segments.

FIG. 7 is a flow chart of a method for identifying and selecting overwrite candidate segments. A new event is detected at block 401. If episode record storage is enabled for the type of event detected, and segments are available in the episode record, as determined at block 402, an entry is made in the episode record at block 403. The allocation table is updated at block 444 to provide a link between the episode record entry and an episode log entry.

If the episode record memory is full or the required number of segments needed to store an episode record entry corresponding to the event type is not available, method 400 proceeds to block 404 to identify a primary overwrite candidate. The primary overwrite candidate is identified as the episode record satisfying rules for identifying an episode record considered to be of least clinical interest. The rules established for selecting overwrite candidates may vary between embodiments. The rules are generally defined to enable identification of events considered to be less clinically important than other stored records. The rules may include a set of prioritized rules for identifying primary and secondary overwrite candidates.

In one embodiment, the first rule is applied at block 404 for determining if any episode records presently stored correspond to an event type for which episode record storage is currently disabled. If such an episode record exists, it is identified as the primary overwrite candidate at block 416. If more than one such episode exists, the oldest of such episodes is identified as the primary overwrite candidate at block 416.

If no episodes exist for which episode record storage has been disabled, method 400 proceeds to block 406 to apply the next rule for identifying overwrite candidates. At block 406, the oldest stored episode is identified. If a predetermined number of episode record entries of the same event type will remain after the oldest stored episode is overwritten, as determined at block 410, that episode is identified as the primary overwrite candidate at block 416. For example, in one embodiment, an episode record will not be identified as a primary overwrite candidate unless at least three records of the same event type will remain after overwriting the episode record. The number of remaining episode records required may vary between embodiments and may be defined differently for different event types. If the oldest stored episode does not meet the requirement of n remaining stored episodes of the same event type as determined at block 410, the next oldest episode record is examined at block 412 until an episode record is identified satisfying the requirement at block 410.

If the episode record identified as the primary overwrite candidate includes the same number of segments required to store the newly detected episode as determined at block 418, the new episode record entry is stored at block 420 by overwriting the primary overwrite candidate. The allocation table is updated at block 422 to link the new episode record entry with the new episode log entry for the detected event. The link between the episode record and the episode log entry corresponding to the overwritten episode is broken.

If some segments are available at the time of episode detection but not enough to store the episode record, and if the primary overwrite candidate equals the number of segments required as determined at block 418, the new episode may be stored by overwriting the primary overwrite candidate at block 420. The available, previously unused segments remain unused and free for storing future episodes.

If the primary overwrite candidate includes more segments than needed, as determined at block 424, the new episode is stored at block 428 by overwriting the portion of the primary candidate segments required. The excess segments included in the primary overwrite candidate not needed to store the new episode are marked as unused at block 430. The available, previously unused segments remain unused and free for storing future episodes.

The allocation table is updated accordingly at block 422. The allocation table is updated at block 422 to link the newly stored episode record entry with the newly logged event and break the link between an episode log entry corresponding to the overwritten episode record entry.

Alternatively, if the primary overwrite candidate in combination with any unused segments includes more segments than required to store the new episode (block 424), the new record may be stored by writing first to the previously unused, available segment(s) and then overwriting to a portion of the segments included the primary overwrite candidate (block 420). The allocation table is updated at block 422 to link the new episode record entry with the newly logged event, and the link to the overwritten episode record entry is broken. Any unused segments of the primary overwrite candidate are marked as available for storing future episode records.

If the primary overwrite candidate involves fewer segments than required to store the new episode (a yes result at decision block 424), a secondary overwrite candidate is identified at block 436. A secondary overwrite candidate may be a second episode record corresponding to an event type that is no longer enabled for episode storage. If no such episodes exist, the next oldest episode is identified for which at least a predetermined number of stored episodes will remain if the episode is overwritten. If the secondary overwrite candidate involves at least the required number of segments (block 438), the secondary candidate is selected and overwritten by the new entry at block 440. The primary overwrite candidate remains stored and is not selected to be overwritten. The allocation table is updated accordingly at block 444. The allocation table entry linking the primary overwrite candidate with an episode log remains. The allocation table entry linking the secondary overwrite candidate with an episode log is broken and a new entry is stored linking the new episode record entry with a corresponding new log entry.

If the secondary overwrite candidate does not involve at least the required number of segments needed to store the new episode (block 438), the primary and secondary candidates are overwritten at block 442. Any remaining segments are marked as available. The allocation table is updated accordingly at block 444. Two episode log entries corresponding to the overwritten primary and secondary overwrite candidates will no longer be linked to episode record entries.

Figure 8:
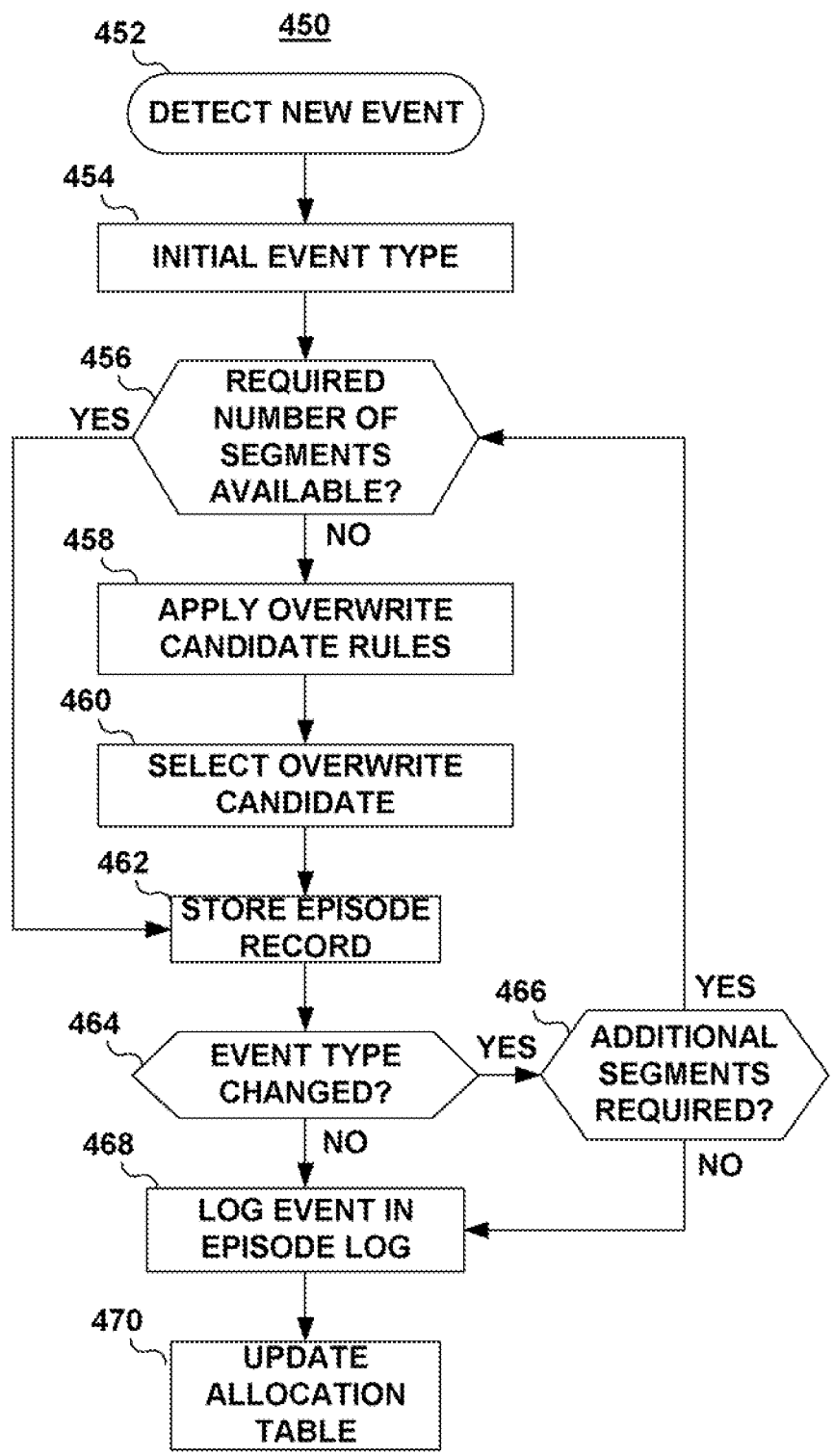
FIG. 8 is a flow chart of a method for storing detected physiological events using dynamic event type categorization and overwrite segment selection.

FIG. 8 is a flow chart of a method 450 for storing detected physiological events using dynamic event type categorization and dynamic overwrite segment selection. At block 452, a new physiological event is detected according to a programmed detection algorithm. The event type is initially categorized at block 454 according to the criteria met for detecting the event. If the required number of episode record segments are available for storing the detected event type, as determined at block 456, the episode record is stored at block 462.

If the required number of segments are not available, rules for identifying primary and secondary overwrite candidates are applied at block 458. The rules applied may be defined specifically for the particular event type. Likewise, rules are applied at block 460 for selecting overwrite candidates to be overwritten, which may also be event type-specific rules. The episode storage begins at block 462 by overwriting the required number of segments for the initially detected event type.

During the episode, the event type may be re-categorized. Other events may be detected during an initially detected event episode causing the event to be re-categorized or a therapy may be delivered causing an event to be re-categorized. For example, if a bradycardia event is initially detected at block 452, but during the episode an asystole is detected, the event may be re-categorized from a bradycardia event to an asystole event. If a VT is initially detected and then discrimination algorithms determine the VT event is actually a supraventricular tachycardia (SVT), the event may be re-categorized as an SVT event. If a VT event is detected that deteriorates into a VF event, the event may be re-categorized, or if a VT event is detected and a therapy is delivered, the event may be re-categorized as a VT treated event.

If the event type remains unchanged as determined at block 464, the episode record entry is completed and the event is logged to the appropriate episode log corresponding to the initially identified event type. If the event type is re-categorized during the episode, however, as determined at block 464, additional segments may be required for storing the episode record entry. If the same number of segments are required, the record entry is completed and the event is logged in the episode log corresponding to the re-categorized event type at block 468. If additional segments are required, however, as determined at block 466, method 450 returns to block 456 to determine if an adequate number of selected overwrite segments remain unused. If so, the episode record entry is written to the unused segments at block 462. If not, the rules for identifying and selecting overwrite candidate segments are applied at block 458 and block 460. Rules applied may be specific to the re-categorized event type.

After storing the episode record entry, an entry is written to the episode log corresponding to the re-categorized event type at block 468. The allocation table is updated at block 470. An allocation table entry is made linking the newly stored episode record entry and the new episode log entry. The links between all overwritten episode record entries and corresponding episode log entries are broken. Any remaining unused segments are marked as available.

In past practice, upon detecting an event, a determination of the event type had to be made upon detection so that physiological data could be written to the portion of memory allocated to storing episode record entries of that event type. By providing a single memory location for storing episode record entries of all event types, storage of the physiological data can begin upon detecting the event, however the final event type does not need to be determined immediately, and can be changed while the episode is in progress. Only the episode log entry, which can be stored after detecting event termination, is written to an episode log separately allocated for the finally determined event type.

Figure 9:
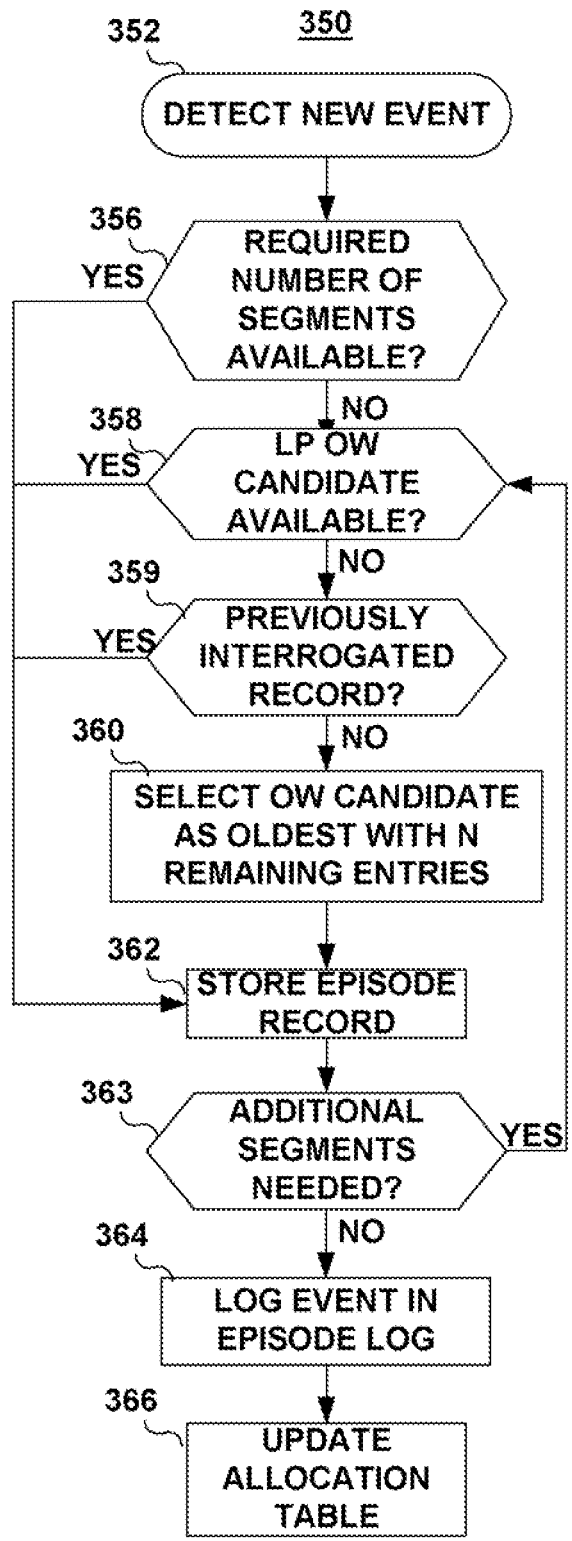
FIG. 9 is a flow chart of an alternative method for storing episode records.

FIG. 9 is a flow chart of an alternative method for storing episode records. In method 400, rules applied for identifying overwrite candidates related to how old the entry was and if other entries for the same event type remained. In other embodiments, the events may be prioritized such that episode record entries corresponding to lower priority event types are preferentially identified as overwrite candidates before identifying episode record entries corresponding to higher priority event types.

In method 350, a new event is detected at block 352 and logged in the appropriate episode log at block 354. If the required number of segments are available in the episode record for writing an episode record entry, as determined at block 356, the episode record entry is stored at block 362. If not, rules are applied for determining if a low priority overwrite (LP OW) candidate is available at decision block 358. For example, in one embodiment, an IMD may be configured for identifying six types of arrhythmia with three types of arrhythmias, e.g. ventricular arrhythmias given high priority, and three types of arrhythmias, e.g. atrial arrhythmias, giving low priority.

At block 358, the oldest, low priority episode record entry is identified for which, if overwritten, a required number of episode record entries of the same event type will remain. The oldest, low priority entry may not be the oldest episode record entry but is identified as a primary overwrite candidate before other higher priority entries. If a low priority entry meets the requirement of n remaining entries after being overwritten, it is selected as the overwrite candidate and is overwritten at block 362.

If no low priority entries can be identified as overwrite candidates based on the "n remaining entries" criteria applied at block 358, any episode record entries that have been previously uplinked to an external device during an interrogation session are identified as primary overwrite candidates at block 359. If a stored record entry has been previously interrogated, it may be overwritten, regardless of event type priority, by a new episode record entry. As such, the oldest of previously interrogated stored episode record entries is selected as an overwrite candidate at block 359 and is overwritten at block 362 by the new episode record entry. In some embodiments, the "previously-interrogated" criteria applied at block 359 may be applied prior to the "n remaining records" criteria applied at block 358 to low-priority record entries.

If no low priority entries meet the requirement of n remaining entries and no previously interrogated entries exist, the oldest overwrite candidate meeting the required n remaining entries is selected as the overwrite candidate at block 360. This overwrite candidate may correspond to a high priority event.

After identifying the primary overwrite candidate, the episode record entry is stored by overwriting the primary overwrite candidate at block 362. If the primary overwrite candidate does not involve the required number of segments to initially write the new record entry, one or more secondary overwrite candidates may be identified using the same prioritized rules until the initially-determined number of segments required to write the episode record entry are identified.

Additional segments may become needed as the episode is in progress. If additional segments become needed for storing the episode, as determined at block 363, additional overwrite candidates can be identified "on-the-fly" by returning to decision block 358. Additional segments may become needed in at least two ways. First, as described above, an episode may be initially detected as one event type requiring a specified number of segments and then reclassified as another event type as the episode progresses, requiring a greater number of segments than the initially detected event type. Second, an event type may be designated a variable number of segments for episode record storage, between some minimum number of segments and some maximum number of segments. For example a VT episode may be designated a minimum of four segments up to a maximum of eight segments. Initially, the minimum number of overwrite segments may be identified and selected according to prioritized overwrite rules. The minimum number of segments may be adequate, e.g. for a relatively short duration episode. If the episode is relative long in duration, however, more segments than the minimum number of segments will be needed as determined at block 363. As such, additional overwrite candidates are selected by returning to block 358 and applying the prioritized rules for identifying and selecting overwrite candidates to free up additional segments for storing the record entry.

After storing the episode record entry, the event is logged in the appropriate episode log at block 364, according to the final determined event type. The allocation table is updated at block 366 to link the new record entry to the episode log entry, break a link between an overwritten record entry and corresponding log entry, and mark any leftover, unused segments as unused.

Figure 10:
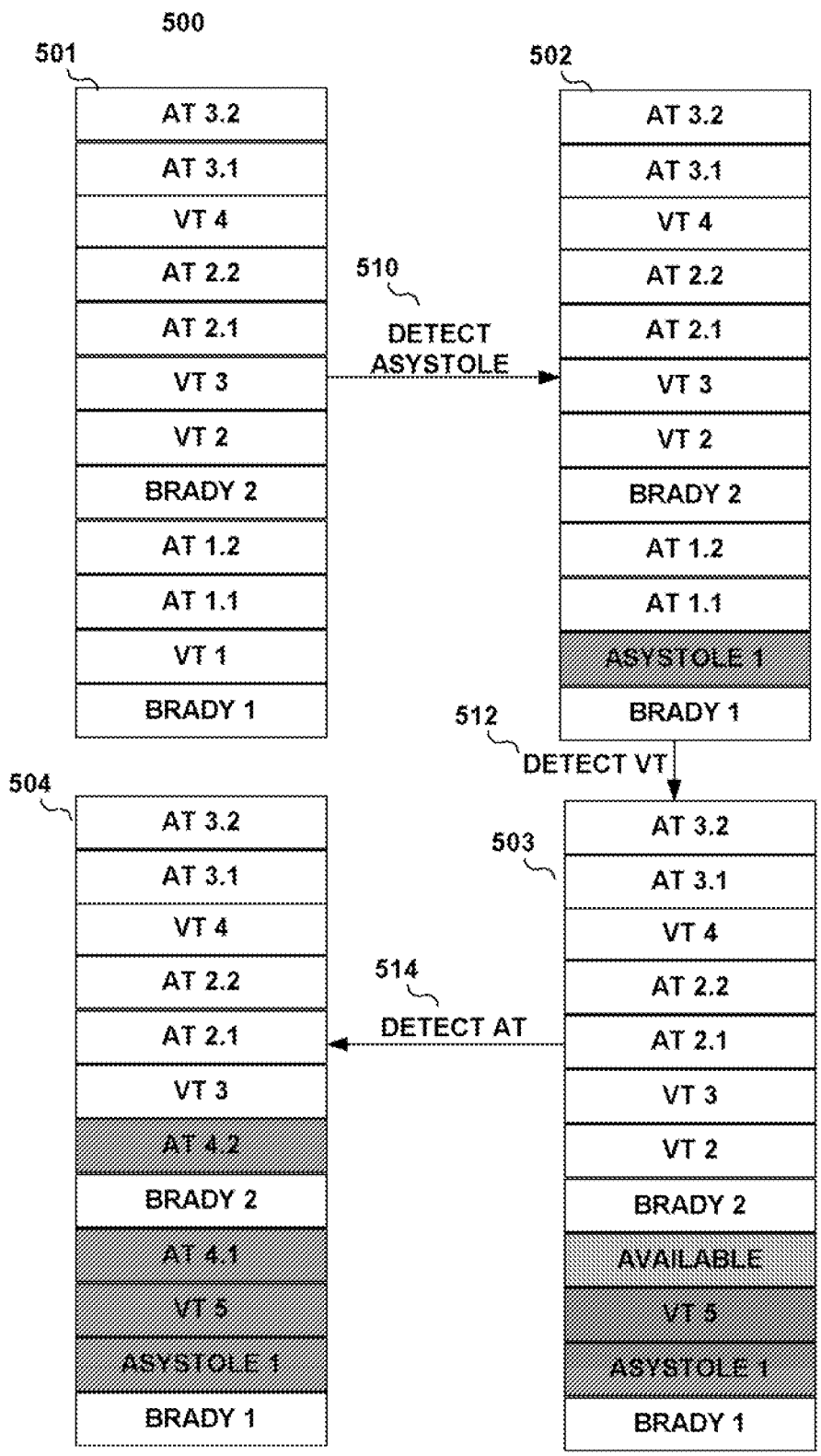
FIG. 10 is a schematic diagram illustrating the process of identifying, selecting and overwriting episode records.

FIG. 10 is a schematic diagram illustrating the process of identifying, selecting and overwriting episode records. In this simplified example, episode record 500 includes 12 segments allocated for storing episode record entries. Each segment is shown occupied at 501. All segments have been filled chronologically as physiological events have been detected beginning at the bottom-most segment in which a bradycardia episode (BRADY 1) has been stored. Next a VT episode (VT 1) is stored. Each of the VT 1 and BRADY 1 events require one segment for episode record storage. The VT 1 episode is followed by an AT episode (AT 1.1 and AT 1.2) which requires two segments for episode storage. The remaining segments are filled with subsequently detected events as indicated, including another bradycardia episode (BRADY 2), three VT episodes (VT 2, VT 3, and VT 4) and two more AT episodes (AT 2.1, AT 2.2 and AT 3.1, AT 3.2).

At a later time, a new episode is detected corresponding to an asystole event 510. The asystole episode record entry requires one segment. Assuming episode record storage remains enabled for all of the event types currently stored, the oldest event having a predetermined number of remaining episode records is identified as a primary overwrite candidate. In this simplified example, event types are not prioritized. In one embodiment, a minimum of two records must remain after overwriting an episode in order to identify the episode as an overwrite candidate. In the example shown, only two bradycardia episodes have been stored. As such, the oldest stored episode, BRADY 1, does not qualify as an overwrite candidate. The next oldest episode record, VT 1, is identified as the primary overwrite candidate because at least two VT episode records (VT 2, VT 3 and VT 4) will remain if VT 1 is overwritten. As such, at 502, the VT 1 episode has been overwritten by a new asystole episode record entry (ASYSTOLE 1).

The next event detected is a VT event at 512. One segment is required for storing a VT episode record entry. The oldest record (BRADY 1) still does not qualify as a primary overwrite candidate because less than two bradycardia episode record entries will remain. The next oldest record is now the AT record stored in two segments AT 1.1 and AT 1.2. If this record is overwritten, two AT episode records (AT 2 and AT 3) will remain. As such, the AT 1 episode is the primary overwrite candidate. The new VT episode (VT5) is stored at 503 by overwriting one of the two AT 1.1 and AT 1.2 segments with the second segment being marked as available.

The next detected event is an AT event at 514. Two segments are required to store an AT episode. Only one segment is currently available as shown at 503. The oldest and the next oldest episode record entries, BRADY 1 and BRADY 2, respectfully, do not qualify as overwrite candidates because if either one was overwritten less than two remaining episodes of the same type would be stored. The next oldest episode record entry is a VT episode (VT 2). If the VT 2 event is overwritten, two VT episode records, VT 3 and VT 4 will remain. As such VT 2 is identified as the primary overwrite candidate. Along with the one available segment, the primary overwrite candidate VT 2 provides the two segments needed to store the new AT episode. The new AT episode is stored at 504 in discontinuous segments AT 4.1 and AT 4.2

It is understood that the methods described in conjunction with FIGS. 7, 8 and 9 and illustrated in FIG. 10 are intended to be illustrative and not limiting. Numerous variations will occur in different implementations of the methods described herein wherein the event types, number of event types, number of segments required to store each event type, and rules for identifying and selecting overwrite candidate records will vary between applications.

Figure 11:
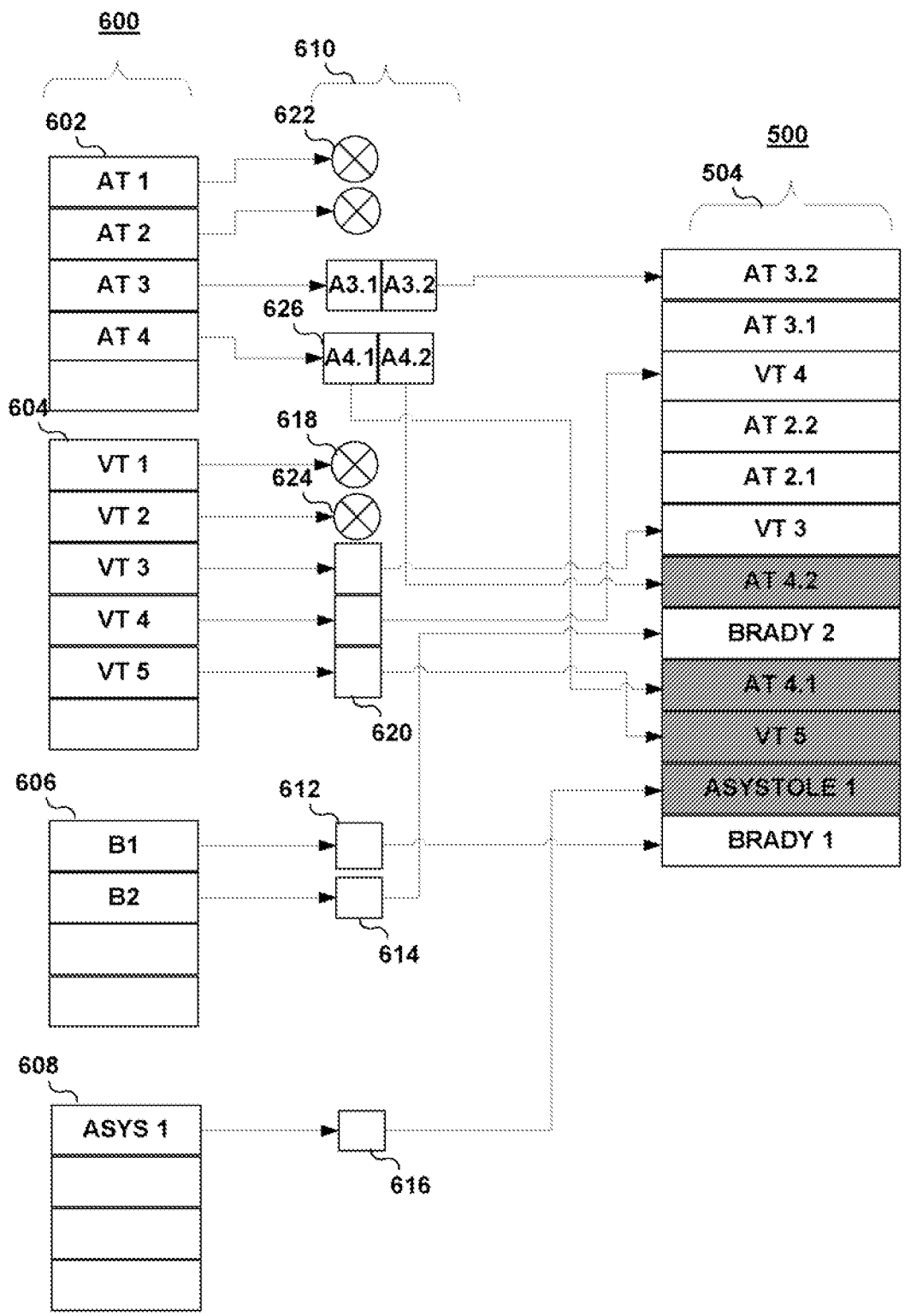
FIG. 11 is a schematic diagram illustrating an episode log and allocation table corresponding to an episode record as shown in FIG. 10.

FIG. 11 is a schematic diagram illustrating an episode log and allocation table corresponding to the episode record at 504 in FIG. 10. Log 600 includes separately allocated episode logs corresponding to the different types of arrhythmia events, namely an AT episode log 602, a VT episode log 604, a bradycardia episode log 606 and an asystole episode log 608. Each episode log is allocated enough memory to store a desired number of log entries, with each entry corresponding to a detected event and including designated data fields for storing summary data as described previously.

Episode record 500 is provided for storing episode records for all event types stored in episode logs 602 through 608 and corresponds to episode record 500 shown in FIG. 10. Episode record 500 is shown having 12 segments occupied as described in conjunction with FIG. 10 at a time 504. Allocation table 610 includes entries for linking episodes logged in episode logs 602 through 608 with corresponding episode record entries stored in episode record 500.

Episode logs 602 through 608 include enough memory to store up to, for example, 30 entries. The number of entries per episode log may be defined differently for each log based on event type. Event types considered to be relatively rare compared to other event types may be allocated a smaller episode log. While illustrative examples provided herein have shown three and four episode logs, it is recognized that any number of episode logs may be provided as appropriate for a particular application. When an episode log 602 through 608 becomes full, a new event will be logged by overwriting the oldest logged event in a particular episode log.

Episode record 500 is allocated enough memory to store, for example, about 20 to 100 segments with each segment storing anywhere from a few seconds of physiological signal data up to one minute of data or more. The overwrite tempo for the episode record 500 will generally be faster than that of any of the episode logs 602 through 608. As illustrated in FIG. 10, several episode records have been overwritten prior to filling any of the individual episode logs 602 through 608.

Beginning with the oldest episode entry BRADY 1 stored in episode record 500, an entry 612 in allocation table 610 links the episode record entry with the logged event B1 in bradycardia episode log 606. A later-occurring bradycardia episode BRADY 2 is linked by allocation table entry 614 to the B2 entry in episode log 606.

A relatively recent asystole event is logged in asystole log 608 (ASYS 1) and linked to the corresponding episode record entry (ASYSTOLE 1) via allocation table entry 616. Referring back to FIG. 10, the asystole event was the first event detected after filling the episode record 500 and caused an overwrite of the first VT event, VT 1, logged in VT episode log 604. As such the allocation table link between the VT 1 log and episode record 500 is broken at 618.

The next event detected after the asystole event was a new VT event, VT 5, which caused an overwrite of one segment of a previously stored AT event, AT1. The allocation table includes an entry 620 linking the logged VT 5 entry in VT episode log 604 with the VT 5 episode record entry. The allocation table link 622 between the AT 1 event logged in AT episode log 602 and the episode record 500 is broken.

The next new event was an AT event, AT 4, requiring two segments for episode record storage. As described above in conjunction with FIG. 10, one available segment that was not used in storing the previously detected VT 5 event and the next primary overwrite candidate, which was identified as the VT 2 event, were overwritten to store the AT4 episode record in two segments, AT 4.1 and AT 4.2. As such, the allocation table link 624 between the VT 2 entry in VT episode log 604 and episode record 500 is broken. A new allocation table entry 626 links the new AT 4 log entry in AT episode log 602 to the two segments AT 4.1 and AT 4.2 in episode record 500. Other previously stored entries in episode record 500, which have not yet been overwritten, namely AT 3 (stored in two segments AT 3.1 and AT 3.2) and VT 3 and VT 4, remain linked to log entries in respective AT episode log 602 and VT episode log 604 by respective entries in allocation table 610.

Upon interrogation of the IMD, data stored in episode logs 602 through 608 can be presented to a clinician with corresponding data stored in episode record 500. Some episode log entries will no longer have links to episode record 500 such that only summary data can be presented. The memory structure and methods described herein thus allow full utilization of memory allocated for storing episode records while maintaining correspondence between episode log entries and episode record entries.

Thus, an implantable medical device system and associated methods for storing physiological signal data have been presented in the foregoing description with reference to specific embodiments. Specific embodiments described herein have related particularly to cardiac-related monitoring. It is recognized that other embodiments may be implemented in other types of implantable medical devices configured for monitoring other types of physiological signals and events, for example neurological monitoring, blood chemistry monitoring, etc. It is appreciated that various modifications to the referenced embodiments may be made without departing from the scope of the invention as set forth in the following claims.

The invention claimed is:

1. A method for storing physiological data in an implantable medical device, comprising:
   separately allocating a plurality of first memory locations to each of a plurality of physiological event types;
   allocating a second memory location to all of the plurality of physiological event types;
   detecting a physiological event of an event type;
   storing event data in a memory location of the plurality of first memory locations corresponding to the event type;
   storing an entry of physiological signal data in the second memory location; and
   entering a location of the entry in an allocation table field linked to the stored event data in the memory location of the plurality of first memory locations, wherein storing the entry comprises overwriting a previously stored physiological signal data entry in response to the second memory location being full, and wherein overwriting the previously stored physiological signal data entry comprises identifying an oldest stored entry of physiological data of an event type for which at least a predetermined number of previously stored physiological data entries of the same event type as the oldest stored entry will remain if the oldest stored entry is overwritten.

2. The method of claim 1 wherein storing the entry comprises applying a set of rules for identifying the previously stored physiological signal data entry to be overwritten.

3. The method of claim 2 wherein the rules for identifying correspond to the event type of the detected physiological event.

4. The method of claim 1 wherein identifying the oldest stored entry further comprises identifying the oldest stored entry of an event type corresponding to a previously defined low priority event type.

5. The method of claim 1 wherein overwriting the previously stored physiological signal data entry comprises identifying a previously stored entry of physiological data that has been previously uplinked to an external device.

6. The method of claim 1 wherein allocating the second memory location comprises dividing the second memory location into a plurality of memory segments and wherein storing the entry further comprises determining a number of the memory segments required for storing the entry, wherein the number corresponds to the event type of the detected physiological event.

7. The method of claim 6, further comprising determining the number of required memory segments as the physiological event is occurring.

8. The method of claim 1 further comprising determining a new event type during the detected physiological event and wherein storing event data comprises storing event data in a memory location of the plurality of first memory locations corresponding to the new event type in response to determining the new event type.

9. The method of claim 8 wherein allocating the second memory location comprises dividing the second memory location into a plurality of memory segments, and wherein storing the entry further comprises determining a number of the memory segments required for storing the entry, wherein the number corresponds to the event type of the detected physiological event, and further comprising re-determining the number of memory segments required for storing the entry in response to determining a new event type.

10. A method for storing physiological data in an implantable medical device, comprising:
separately allocating a plurality of first memory locations to each of a plurality of physiological event types;
allocating a second memory location to all of the plurality of physiological event types;
detecting a physiological event of an event type;
storing event data in a memory location of the plurality of first memory locations corresponding to the event type;
storing an entry of physiological signal data in the second memory location; and
entering a location of the entry in an allocation table field linked to the stored event data in the memory location of the plurality of first memory locations, wherein storing the entry comprises overwriting a previously stored physiological signal data entry in response to the second memory location being full, wherein overwriting the previously stored physiological data entry further comprises overwriting a second previously stored entry of physiological data, and wherein overwriting the second previously stored entry comprises identifying a next oldest stored entry of physiological data of a next event type for which at least a predetermined number of previously stored entries of the next event type will remain if the next oldest stored entry is overwritten.

11. An implantable medical device configured to detect physiological events, comprising:
a plurality of first memory locations separately allocated to each of a plurality of physiological event types;
a second memory location allocated for storing entries of physiological signal data corresponding to all of the plurality of physiological event types;
an allocation table forming a plurality of fields; and
a control module configured to store event data in a memory location of the plurality of first memory locations in response to detecting a physiological event of a first event type, the memory location of the plurality of first memory locations corresponding to the first event type, store an entry of physiological signal data in the second memory location, and enter a location of the stored entry of physiological signal data in an allocation table field linked to the stored event data in the memory location of the plurality of first memory locations, wherein storing the entry of physiological signal data comprises overwriting a previously stored entry of physiological signal data in response to the second memory location being full, and wherein the control module identifies the previously stored entry as an oldest stored entry of an event type for which at least a predetermined number of previously stored entries of the same event type as the oldest stored entry will remain if the oldest stored entry is overwritten.

12. The implantable medical device of claim 11 wherein the control module applies a set of rules for identifying the previously stored physiological signal data entry to be overwritten.

13. The implantable medical device of claim 12 wherein the rules for identifying correspond to the event type of the detected physiological event.

14. The implantable medical device of claim 11 wherein identifying the previously stored entry comprises identifying the oldest stored entry of an event type corresponding to a previously defined low priority event type.

15. The implantable medical device of claim 11 wherein the control module identifies the previously stored entry as an entry that has been previously uplinked to an external device.

16. The implantable medical device of claim 11 wherein the second memory location comprises a plurality of memory segments, and wherein storing the entry comprises determining a number of the memory segments required for storing the entry, wherein the number corresponds to the event type of the detected physiological event.

17. The implantable medical device of claim 16 wherein the control module is configured to determine the number of required memory segments as the physiological event is occurring.

18. The implantable medical device of claim 11 wherein the control module determines a new event type during the detected physiological event and wherein storing event data comprises storing event data in a memory location of the plurality of first memory locations corresponding to the new event type in response to determining the new event type.

19. The implantable medical device of claim 18 wherein the second memory location comprises a plurality of memory segments and wherein storing the entry comprises determining a number of the memory segments required for storing the entry, wherein the number corresponds to the event type of the detected physiological event, the control module being configured to re-determinine the number of memory segments required for storing the entry in response to determining a new event type.

20. An implantable medical device configured to detect physiological events, comprising:
a plurality of first memory locations separately allocated to each of a plurality of physiological event types;
a second memory location allocated for storing entries of physiological signal data corresponding to all of the plurality of physiological event types;
an allocation table forming a plurality of fields; and
a control module configured to store event data in a memory location of the plurality of first memory locations in response to detecting a physiological event of a first event type, the memory location of the plurality of first memory locations corresponding to the first event type, store an entry of physiological signal data in the second memory location, and enter a location of the stored entry of physiological signal data in an allocation table field linked to the stored event data in the memory location of the plurality of first memory locations, wherein storing the entry of physiological signal data comprises overwriting a previously stored entry of physiological signal data in response to the second memory location being full, wherein overwriting the previously stored entry further comprises overwriting a second previously stored entry and wherein the control module identifies the second previously stored entry as a next oldest stored entry of a next event type for which at least a predetermined number of previously stored entries of the next event type will remain if the next oldest stored entry is overwritten.

21. A non-transitory computer-readable medium having computer-executable instructions for performing a method comprising:
  allocating a plurality of first memory locations separately to each of a plurality of physiological event types;
  allocating a second memory location to all of the plurality of physiological event types;
  detecting a physiological event of an event type;
  storing event data in a memory location of the plurality of first memory locations corresponding to the event type;
  storing an entry of physiological signal data in the second memory location; and
  entering a location of the stored entry of physiological signal data in an allocation table field linked to the stored event data in the memory location of the plurality of first memory locations, wherein storing the entry comprises overwriting a previously stored physiological signal data entry in response to the second memory location being full, and wherein overwriting the previously stored physiological signal data entry comprises identifying an oldest stored entry of physiological data of an event type for which at least a predetermined number of previously stored physiological data entries of the same event type as the oldest stored entry will remain if the oldest stored entry is overwritten.

22. An implantable medical device configured to detect physiological events, comprising:
  a plurality of first memory locations separately allocated to each of a plurality of physiological event types;
  a second memory location allocated for storing entries of physiological signal data corresponding to detected episodes of all of the plurality of physiological event types;
  an allocation table comprising a plurality of fields; and
  a control module configured to store event data in a memory location of the plurality of first memory locations in response to detecting a physiological event of a first event type, the memory location of the plurality of first memory locations corresponding to the first event type, store an entry of physiological signal data corresponding to the detected physiological event in the second memory location, and enter a location of the stored entry of physiological signal data in an allocation table field linked to the stored event data in the memory location of the plurality of first memory locations, wherein storing the entry of physiological signal data comprises overwriting a previously stored entry of physiological signal data in response to the second memory location being full, and wherein the control module identifies the previously stored entry as an oldest stored entry of an event type for which at least a predetermined number of previously stored entries of the same event type as the oldest stored entry will remain if the oldest stored entry is overwritten.

* * * * *